United States Patent [19]

Ruhenstroth-Bauer et al.

[11] 4,330,528
[45] May 18, 1982

[54] DRUG FOR STIMULATING THE RATE OF PROLIFERATION OF LIVER CELLS AND METHOD FOR PRODUCING SAME

[75] Inventors: Gerhard Ruhenstroth-Bauer, Gräfelfing; Michel Goldberg, Munich, both of Fed. Rep. of Germany

[73] Assignee: Max-Planck-Gesellschaft zur Foerderung der Wissenschaften E.V., Fed. Rep. of Germany

[21] Appl. No.: 105,923

[22] Filed: Jul. 3, 1980

Related U.S. Application Data

[63] Continuation of Ser. No. 44,886, Jun. 4, 1979, abandoned.

[30] Foreign Application Priority Data

Apr. 12, 1979 [DE] Fed. Rep. of Germany ....... 2914903

[51] Int. Cl.³ .................... A61K 35/14; A61K 37/00; A61K 35/407; C07G 00/00
[52] U.S. Cl. .................... 424/101; 260/112 R; 424/106; 424/177
[58] Field of Search ............ 424/101, 106, 177; 260/112 R

[56] References Cited

U.S. PATENT DOCUMENTS

| 2,045,266 | 6/1936 | Fenger | 260/112 R |
| 2,710,293 | 6/1955 | Gerlough | 260/112 B |
| 3,583,968 | 6/1971 | Pien | 260/112 R |
| 3,718,541 | 2/1973 | Kalina | 260/112 R |
| 3,876,774 | 4/1975 | Fortini et al. | 424/177 |
| 3,880,989 | 4/1975 | Garcia | 424/101 |
| 3,994,870 | 11/1976 | Newaith | 260/112 B |
| 4,024,247 | 5/1977 | Fortini et al. | 424/177 |
| 4,027,013 | 5/1977 | Bick et al. | 260/112 B |
| 4,054,557 | 10/1977 | Sievertsson et al. | 260/112 R |
| 4,057,628 | 11/1977 | Bick | 424/101 |

FOREIGN PATENT DOCUMENTS

| 2426584 | 9/1975 | Fed. Rep. of Germany | 424/106 |
| 7722M | 3/1970 | France | 424/106 |
| 565986 | 12/1944 | United Kingdom | 424/106 |

OTHER PUBLICATIONS

Bauer et al.-Hoppe-Seyler's Z. Physiolo. Chem. Bd., 359, 5 543-545, (1978).

*Primary Examiner*—Douglas W. Robinson
*Attorney, Agent, or Firm*—Keil & Witherspoon

[57] ABSTRACT

A drug for stimulating the rate of proliferation of liver cells having as its active ingredient a blood plasma extract (NP) and a method of preparing such a drug wherein blood plasma is first acidified to a pH of 5.5, then heat denatured at approximately 95° C. and subsequently centrifuged to provide the extract.

3 Claims, No Drawings

DRUG FOR STIMULATING THE RATE OF PROLIFERATION OF LIVER CELLS AND METHOD FOR PRODUCING SAME

CROSS REFERENCE TO RELATED DISCLOSURES

This application is a continuation of application Ser. No. 44,886 filed June 4, 1979, now abandoned.

BACKGROUND OF THE INVENTION

The invention relates to a drug for stimulating the rate of proliferation of liver cells, a liver protection and growth factor, and a method for producing them.

The extraction of a liver growth factor from the livers of partially hepatectomized rats is already known. Such a factor is a protein or proteide containing no amount of neuraminic acid of significance to the activity and having a molecular weight of between 30,000 and 50,000 D. The effect of this factor is organ-specific, but not species-specific. See Ruhenstroth-Bauer, Goldberg, Silz and Strecker, *Hoppe-Seyler's Z. Physiol. Chem.* 359, 543–545 (April, 1977); also see the earlier German patent application No. P 28 14 981.7-41 of Apr. 7, 1978 (corresponding to U.S. patent applications Ser. Nos. 973,666 and 028,304, both abandoned and 130,648, now allowed. As further prior art, see Demetriou, A. A. and Levenson, S. M., Annual Meeting of the American Association for the Study of Liver Disease, Nov. 6–8, 1978, Chicago, Ill., page 959. The subject of the earlier patent application is the extraction of a preliminary factor from the plasma of animals having partially hepatectomized livers, from which a liver growth factor can be split off by means of treatment with neuraminidase or neuramyltransferase. From this process of obtaining the liver growth factor, the following function model can be derived: The partially hepatectomized liver sends out a stimulus of some kind or other which, in a manner not yet known in detail, leads to the existence of the preliminary factor in the blood plasma. Then, by means, for example, of neuraminidase, which is present in increased amounts in the blood of partially hepatectomized animals, the preliminary factor is converted into the actual liver growth factor which causes proliferation of the liver cells.

OBJECT AND SUMMARY OF THE INVENTION

The object which is the basis of the invention is to isolate further liver growth factors.

The invention further pertains to the liver growth factors per se and to a method of producing them.

The liver growth factors are accordingly derived from the blood plasma of animals which have not been partially hepatectomized. The invention makes use of the new concept that, in addition to the governing system described above, there is a second governing system for liver growth independent of the first, which is provided by means of a substance which is always present in the blood plasma rather than only after partial hepatectomy (factor derived from the plasma of normal animals=NP). As a result of the action of trypsin-chymotrypsin, this factor is converted into a highly active liver growth factor (plasma from normal animals treated with trypsin-chymotrypsin=NPTC). These two liver growth factors may be designated as parts of a "second" governing system which is independent of the first governing system as it is disclosed in the earlier German patent application No. P 28 14 981.7-41.

Thus, by means of an acid-heat extraction of the blood plasma, one obtains the first of the two new liver growth factors, which comprises one or more proteins.

This NP extract itself already has the effect of somewhat activating proliferation. When treated with trypsin-chymotrypsin, these proteins yield one or more peptides, which act in a manner to activate the rate of proliferation in an extraordinary way. In contrast, the liver growth factor according to the older German patent application No. P 28 14 981.7-41, derived from partially hepatectomized animals, is a protein or proteide which is destroyed by an enzymatic treatment with trypsin-chymotrypsin.

The fact that the NP extract, which is derived from the blood plasma by means of acidification and heat denaturation, already displays a certain proliferation activity may be ascribed to a property of the proteins themselves, or it may be that the peptides contained in the NPTC factor are already present in a certain quantity in the NP extract, possibly bonded to the proteins.

As noted, the NP extract of normal animals which has not yet been treated with trypsin-chymotrypsin already displays a certain proliferation activity which is greater than that in the (saline solution) control values. The activity of the NPTC extract treated with trypsin-chymotrypsin is significantly higher. Typically, peptide-peptidyl hydrolases such as trypsin-chymotrypsin split peptide bonds or peptide chains apart into individual peptides. Treatment of this highly effective liver growth factor NPTC with pronase, an enzyme which further breaks down peptides, results in a complete loss of the proliferation activity. It may be determined therefrom that the new liver growth factor is a peptide.

That this new governing system is one which is independent from the known governing system may be determined in that treatment of the new liver growth factor with neuraminidase or $\beta$-galactosidase does not affect its activity. That is, a neuraminic acid is not split off by treatment with neuraminidase and the remainder activated, as is the case with the already known "first" liver growth factor. Since, in addition, neuraminic acid is generally coupled to $\beta$-galactose, which is taken up by appropriate receptors in the liver after the neuraminic acid is split off, a factor based on this known model would have to become inactive if the $\beta$-galactose is split off by means of $\beta$-galactosidase. This is, however, not the case with the new liver growth factor.

As is described below in further detail, the active ingredient contained in the NP extract may be qualitatively characterized as a protein or a proteide; however, its most important characterization is to be seen in that the active ingredients contained in the NPTC extract which can be characterized substantially more precisely arise as a result of the action of trypsin-chymotrypsin.

DETAILED DESCRIPTION

The new liver growth factor is obtained as follows:

The blood plasma of normal rats is removed. The experiments were performed using female, specifically pathogen-free Wistar rats weighing between 95 and 105 grams (source: Institut für Strahlen- und Umweltforschung, Neuherberg/Munich). After the animals were sacrificed, they were bled and the blood plasma was obtained and prepared as follows:

The heparinized whole blood was centrifuged for 20 minutes at 4000 g and the plasma was pipetted off.

The blood plasma obtained was brought to a pH level of 5.5 with a hydrochloric acid solution at a concentration of 0.1 N. This acidification is an important means of selection for splitting off a large number of proteins: they are precipitated out and thus withdrawn from the further concentration or isolation process. After extraction of the substances precipitated out and thus made inactive, the remaining substance was heat-denatured at a temperature of 95° C. for a period of 20 minutes. In this manner, further components of the plasma, that is, those which are not stable at this temperature and at this pH level, are precipitated out.

By means of the acidification to pH 5.5 and the heat-denaturation, a large proportion of the plasma components is removed. Next, the plasma is centrifuged for a period of 15 minutes with 4000 g (the apparatus used was a Minifuge Christ, Osterode/Harz, Germany). The supernatant, after centrifuging, thus contains only those active ingredients, out of all the ingredients contained in the original plasma, which are stable at both a pH of 5.5 and a temperature of 95° C. However, it contains these in a concentrated form. Now in order to obtain also those portions of these active ingredients which may still be contained in the precipitates resulting from centrifuging, these precipitates were mixed with twice-distilled water to bring them up to the original volume, subjected again to acidification to a pH of 5.5 and to heat-denaturation at 95° C. and finally centrifuged. Altogether, this was repeated twice. Thus, the NP extract was obtained.

The supernatants (NP extracts) of these three centrifuging procedures were mixed together and subjected to the subsequent trypsin-chymotripsin treatment.

150 mg of supernatants were mixed with 20 ml of twice-distilled water, brought to pH 7.6 and incubated at 30° C. for a period of 2 hours with 80 U of trypsin, purest grade, and 90 U of α-chymotrypsin, purest grade (source: Serva, Heidelberg).

Next, in order to deactivate the remaining active enzymes, it was incubated for a period of 30 minutes at 95° C. and subsequently centrifuged. In this manner, the PNTC extract containing the liver growth factor is obtained.

The solution was then lyophilized, dissolved in 2 ml of a 0.9% saline solution and injected intraperitoneally (i.p.) into normal rats. Control animals were injected i.p. with the same quantity of a 0.9% saline solution.

The measurement of liver cell proliferation after injection of the NPTC extract was then undertaken by measuring the synthesis of DNA. This is done by measuring the quantity of radioactive substances specifically incorporated into the DNA, that is, of $^3$H-methylthymidin (special activity, 25 Ci/mmol; source: Radiochem. Center, Amersham).

The experimental animals and the control animals were injected with 50μ Ci of $^3$H-methylthymidin 19 hours after the injection of the NPTC extract. One hour later, the animals were sacrificed. The liver was removed and stored at −20° C.

Extraction of the liver DNA was then performed in accordance with the procedure of Weinbren, K. and Woodward, E. (*Br. J. Exp. Path.* 45,442–449 (1964)). A portion of this extract was used for a measurement of radioactivity. To this end, 1.5 ml of the PCA (perchloracetic acid) solution was neutralized with 0.5 ml NaOH at a concentration of 1 N. The resultant solution was mixed in a scintillation tube with 5 ml Triton X and 10 ml toluol (0.6 PPO; PPO=1,5-diphenyloxazole).

With the aid of a liquid scintillation counter (source: Intertechnique, Paris), the radioactivity was then determined as the number of disintegrations per minute. A further portion of the DNA extract was used for measurement of the DNA concentration in accordance with Burton (*Biochem. J.* 62, 315–323 (1956)). Thus, as a standard for DNA synthesis, one obtains the specific activity in disintegrations per minute per microgram of DNA.

On the average, the normal rats injected with NPTC extract showed, under the experimental conditions cited, an average specific activity of 372±95 disintegrations per minute per microgram of DNA (number of experimental animals: n=8).

The normal rats injected with the NP extract showed, under the same conditions, an average specific activity of 170±36 disintegrations per minute per microgram of DNA (n=6).

In the normal rats injected with a physiological saline solution, a value of 105±22 disintegrations per minute per microgram of DNA (n=8) was obtained.

The NP extract derived from the normal blood plasma, without trypsin-chymotrypsin treatment, already shows an increased activity. The NPTC extract produces an increase by the factor of 3.5, and with great statistical accuracy ($p<0.01$).

Thus, it is demonstrated that the i.p. injection of the NPTC extract causes a great increase in DNA synthesis in normal animals, which synthesis in turn is a necessary precondition for cell division and thus for liver growth through cell division.

A further experiment demonstrated that the NPTC extract is also proliferation-active in cultures of hepatocytes of adult rats. These cultures were obtained as follows:

Hepatocytes were isolated with collagenase in accordance with the method of G. Williams (in vitro, 13, 809 (1977)), taken from rats weighing between 350 and 450 grams. The cells were washed twice, each time with 10 ml of L-15 medium (source: Boehringer, Mannheim). Subsequently they were suspended in L-15 medium; the final concentration was $2–4 \times 10^5$ cells per milliliter. One ml of this suspension was placed in each Petri dish and 100 μl of fetal calf serum was added to it. After an incubation period of 4 hours (at 37.5° C. and 100% $O_2$), from 5 to 7 μg of a NPTC extract was added to each dish, with a similar amount of physiological saline solution added to the control dishes. After a further 19 hours of incubation, tagging was performed for one hour with 0.5μ Ci $^3$H-thymidine per dish. After being washed six times with a saline solution, the incorporation was stopped with an ice-cold 7% TCA solution; the cells were drawn up onto glass fiber filters and washed first with TCA and then with ethanol. The filters were dried at 120° C. and measured by the method described above in the liquid scintillation counter.

In comparison with the controls, the incorporation of thymidine in the cultures to which NPTC had been added was found to have increased by a factor of 3 to 4 over that in the control cultures.

Qualitatively, the liver growth factor which has been discovered may be characterized as follows:

A treatment of the NPTC extract with pronase caused inactivity. To determine this, a NPTC extract was dissolved in 10 ml of twice-distilled water, brought to a pH of 7.5 and incubated at 37° C. for two hours with 100 U of pronase P (source: Sigma, Munich). In order to inactivate the remaining enzyme activity, it was then incubated for 30 minutes at 95° C. and centrifuged. Subsequently, the solution was lyophilized, dissolved in 2 ml of 0.9% saline solution and injected into normal rats.

The result was a proliferation rate of 75±g disintegrations per minute per microgram of DNA. Since, on the one hand, the high activity had first been produced by a trypsin-chymotrypsin treatment and, on the other hand, it had been destroyed by a pronase treatment, the conclusion may be drawn that the substance is a peptide.

The NPTC extract was further treated with neuraminidase and with galactosidase, as follows:

In order to perform the treatment with beta-galactosidase, a NPTC extract was dissolved in 10 ml of twice-distilled water and incubated for one hour with 5 U of beta-galactosidase (source: Sigma, Munich). In order to inactivate the remaining enzyme activity, the solution was then incubated for 30 minutes at 95° C. and centrifuged. Subsequently the clear solution was lyophilized, dissolved in 2 ml of 0.9% saline solution and injected into normal rats.

In order to perform the treatment with neuraminidase, a NPTC extract was dissolved in 10 ml of twice-distilled water, brought to a pH of 5.5, and incubated at 37° C. for one hour with 250 U of neuraminidase (source: Behringwerke AG, Marburg, Germany). In order to inactivate the remaining enzyme activity, the solution was then incubated for 30 minutes at 95° C. and centrifuged. Subsequently the solution was lyophilized, dissolved in 2 ml of 0.9% saline solution and injected into normal rats.

After both the enzyme treatment with beta-galactosidase and treatment with neuraminidase, the high proliferation activity of the treated NPTC extract did not change.

In order to determine the molecular weight, a G 15 chromatography was performed. Sephadex G 15 was used as the column material (column volume, 121 ml). After equilibrating the column with 50 mM of TRIS buffer at pH 7.6, a NPTC extract, dissolved in 2 ml of the same buffer, was added. The flow rate was 11 ml per hour. Fractions of 5 ml each were collected and the $OD_{280}$ was measured. The individual protein peaks were collected, lypohilized, dissolved in 2 ml of twice-distilled water and injected into normal rats. In order to determine the molecular weight, the following reference substances were added to the column: Glutathion (molecular weight 307), NAD (molecular weight 663), 7-peptide (molecular weight 981). For the active protein peak, a molecular weight of approximately 1200 was obtained.

A NPTC extract was also produced from human blood plasma by the methods described above. The NPTC extract thus obtained from human plasma was injected i.p. into rats. After preparation, a proliferation rate in rats of 410±112 disintegrations per minute per microgram of DNA (n=5) was ascertained.

The conclusion to be drawn from this is that the NPTC is not species-specific. Thus it is permissible to conclude with a high degree of probability, based on the experiments with rats, that the factor also has the same effect in humans.

An examination of the spleen and kidney of the rats after an injection of the NPTC extract yielded proliferation rates of 307±66 disintegrations per minute per microgram of DNA for spleen tissue (the control figures were 354±31) and 51±13 disintegrations per minute per microgram of DNA for kidney tissue (compared with control figures of 43±10) (n=4).

Thus, there was no ascertainable change. The conclusion may therefore be drawn that the liver growth factor described herein is organ-specific.

It is, of course, possible to modify the liver growth factor NP or NPTC, obtained in the described manner, chemically, without its losing its effectiveness. This may be done, for example, by attaching additional groups to individual groups, or by exchanging them with others. The invention therefore also includes equivalent chemical modifications of the NP and NPTC factors.

What is claimed and desired to be secured by Letters Patent of the United States is:

1. A factor for stimulating the rate of proliferation of liver cells formed by a process comprising the steps of
    providing a quantity of blood plasma of normal animals.
    acidifying said blood plasma to a pH level of 5.5,
    heat denaturing said acidified plasma at a temperature of approximately 95° C.,
    centrifuging said acidified and heat denatured blood plasma to remove the denatured proteins from the plasma, and
    treating the supernatant from said centrifugation with a peptide-peptidyl-hydrolase to obtain said factor, said factor being a neuraminic-acid-free and betagalactose-free peptide with a molecular weight of approximately 1200 D.

2. A factor in accordance with claim 1, wherein said peptide-peptidyl hydrolases (NPTC) are trypsin and chymotrypsin.

3. A factor for stimulating the rate of proliferation of liver cells formed by a process comprising the steps of
    providing a quantity of blood plasma of normal animals,
    acidifying said blood plasma to a pH level of 5.5,
    heat denaturing said acidified plasma at a temperature of approximately 95° C.,
    centrifuging said acidified and heat denatured blood plasma to remove the denatured protein from the plasma, and
    treating the supernatant from said centrifugation with trypsin or chymotrypsin to obtain said factor, said factor being a neuraminic-acid-free and betagalactose-free peptide with a molecular weight of approximately 1200 D.

* * * * *

UNITED STATES PATENT AND TRADEMARK OFFICE
CERTIFICATE OF CORRECTION

PATENT NO. : 4,330,528
DATED : May 18, 1982
INVENTOR(S) : GERHARD RUHENSTROTH-BAUER and MICHEL GOLDBERG It is certified that error appears in the above—identified patent and that said Letters Patent is hereby corrected as shown below:

The application number appearing on the first page of the above-identified patent should be corrected from "105,923" to --165,923--.

Signed and Sealed this

Twentieth Day of July 1982

[SEAL]

Attest:

Attesting Officer

GERALD J. MOSSINGHOFF

Commissioner of Patents and Trademarks